(12) United States Patent
Owens

(10) Patent No.: US 6,566,051 B1
(45) Date of Patent: May 20, 2003

(54) LATERAL FLOW TEST STRIP

(75) Inventor: Mitchell Owens, Greensboro, NC (US)

(73) Assignee: Medtox Scientific, Inc., St. Paul, MN (US)

( * ) Notice: Subject to any disclaimer, the term of this patent is extended or adjusted under 35 U.S.C. 154(b) by 0 days.

(21) Appl. No.: 09/889,270

(22) PCT Filed: Jan. 14, 2000

(86) PCT No.: PCT/US00/00990

§ 371 (c)(1),
(2), (4) Date: Jul. 13, 2001

(87) PCT Pub. No.: WO00/42430

PCT Pub. Date: Jul. 20, 2000

Related U.S. Application Data (60) Provisional application No. 60/115,984, filed on Jan. 15, 1999.

(51) Int. Cl.⁷ .................................................. C12Q 1/00
(52) U.S. Cl. ........................... 435/4; 435/287.8; 422/58
(58) Field of Search ......................... 435/4, 287.8, 970; 422/55–58; 436/165, 169, 170, 810

(56) References Cited

U.S. PATENT DOCUMENTS

| | | | | |
|---|---|---|---|---|
| 4,256,693 A | * | 3/1981 | Kondo et al. ................. | 422/56 |
| 4,790,979 A | * | 12/1988 | Terminiello et al. .......... | 422/56 |
| 5,238,652 A | * | 8/1993 | Sun et al. ...................... | 422/61 |
| 6,162,639 A | * | 12/2000 | Douglas .................. | 435/287.1 |
| 6,258,045 B1 | * | 7/2001 | Ray et al. .................... | 600/573 |
| 6,297,020 B1 | * | 10/2001 | Brock ........................ | 435/7.1 |
| 6,297,060 B1 | * | 10/2001 | Nowkowski et al. ........ | 436/518 |
| 6,312,888 B1 | * | 11/2001 | Wong et al. .................... | 435/4 |

FOREIGN PATENT DOCUMENTS

| | | | | |
|---|---|---|---|---|
| EP | 0 443 231 A | * | 8/1991 | |
| EP | 0443231 | | 8/1991 | .......... G01N/33/52 |
| EP | 0459093 | | 12/1991 | ............ C12M/1/32 |
| WO | 95/17965 | | 7/1995 | ............ B01L/3/00 |
| WO | WO 95/17965 | * | 7/1995 | |

* cited by examiner

*Primary Examiner*—Ralph Gitomer
(74) *Attorney, Agent, or Firm*—Fredrikson & Byron, P.A.

(57) ABSTRACT

The present invention provides a test strip having a first layer comprising a wicking member and a second layer comprising a capillary transfer plane member. The capillary transfer plane has a plurality of capillary transfer passages. The capillary transfer passages can comprise various shapes to control sample flow rate. Located above one or more of the capillary transfer passages are a plurality of test strips. Another aspect of the present invention provides a sample testing device, which includes a housing having a one or more openings, and a test strip as described above, wherein a sample application area of the test strip is accessible through one of the openings in the housing, and each of the testing members is viewable through one of the openings of the housing.

31 Claims, 5 Drawing Sheets

MYLAR BACKING = 0.12mm
WICKING PAD = 0.20mm
MYLAR MIDPIECE = 0.16mm
REAGENT PAD = 0.42mm
COMPRESSION = 0%

FIG. 14
SECTION D-D

FIG. 15
SECTION C-C

LATERAL FLOW TEST STRIP

CROSS-REFERENCE TO RELATED INVENTIONS

This application claims the benefit under 35 U.S.C. 120 to PCT application No. WO 00/42430, filed on Jan. 14, 2000, which was published in English as per PCT article 21(2), which in turn claims priority based on provisional U.S. application Ser. No. 60/115,984, filed on Jan. 15, 1999.

FIELD OF THE INVENTION

This invention relates to the field of sample testing systems, and specifically to a lateral flow test strip and apparatus.

BACKGROUND

Testing of bodily fluids for drugs is an increasingly important field because of increased recognition of the need for safety. For example, employers have the need to test employees in dangerous jobs such as construction, truck driving or piloting. Also, testing bodily fluid samples for other purposes, such as disease detection and other diagnostic purposes, is also important.

In the past, assorted systems for collecting and testing samples have been used. For example in one method, when a test is needed, a sample, usually urine, blood, or another bodily fluid, is deposited into a cup. Currently, the user places a dipstick into the collection cup, assuring that all test sites on the dipstick are submerged within the fluid. The dipstick remains in the sample fluid for approximately one second. The dipstick is then removed by dragging it along the edge of the specimen cup to remove excess urine or other fluid. Some type of absorbent paper must be placed on a flat surface, upon which the dipstick will be placed, with test sites up, to absorb all excess fluid. The dipstick must not be left in the collection cup any longer than one second because the chemicals used in the test area will begin to dissolve into the sample, coming off the test area, thereby providing inaccurate test results because of cross-contamination.

Overall, this is an unsanitary process that can result in urine getting onto counter-tops, clothes, instruments, etc. Also, if multiple samples are being tested, as is the case in a laboratory environment, it is difficult to efficiently identify multiple samples once they are removed from the collection cup.

For the reasons stated above, and for other reasons stated below which will become apparent to those skilled in the art upon reading and understanding the present specification, there is a need in the art for a better method and apparatus for performing testing of samples.

SUMMARY OF THE INVENTION

In one embodiment, the present invention provides an a test strip having a first layer comprising a wicking member and a second layer comprising a capillary transfer plane member. The capillary transfer plane member has a plurality of capillary transfer passages. Located above one or more of the capillary transfer passages are a plurality of testing members holding a testing reagent.

In further embodiments, the test strip includes a third layer next to the wicking member for providing support to the wicking member. Other features include capillary transfer passages comprising a hole, channel, or other shape to control sample flow rate.

Another aspect of the present invention provides a sample testing device, which includes a housing having a plurality of openings, and a test strip as described above, wherein each of the testing members viewable through at least one of the plurality of openings of the housing.

Advantageously, the present system provides a test strip that separates the testing member holding the testing reagent from the sample holding member itself. Thus, providing a simpler testing process which helps prevent unsanitary conditions and cross-contamination. The test strip can be placed into a carrier device or instrument to assist in handling and containing the sample being tested, such as urine, blood, body fluids or any other type of sample extraction. The resent invention makes the testing process easier, more sanitary, and less confusing when processing multiple samples.

DESCRIPTION

In the following detailed description, reference is made to the accompanying drawings that form a part hereof, and in which are shown by way of illustration specific embodiments in which the invention may be practiced. It is understood that other embodiments may be utilized and structural changes may be made without departing from the scope of the present invention.

FIGS. 1–6 show one embodiment of a lateral flow test strip 100 according to the present invention. Test strip 100 includes a first layer, such as a wicking member 101, for holding and carrying the sample. Wicking member 101 includes a sample application area 115 and an absorbent area 113. In one embodiment, wicking member 101 is fabricated from an efficient liquid transferring material, such as a wicking membrane material, that allows a sample placed on the sample application area 115 to freely flow to the absorbent area 113. Test strip 100 also includes a capillary transfer plane member 102 and a plurality of assorted test pads or testing members 108–112. In one embodiment, test strip 100 can include a backing layer 114 to provide support for wicking member 101. The backing member 114 may be Mylar or other rigid support material.

Capillary transfer plane member 102 is adhesively attached to one side of the first layer or wicking member 101. It is located so that it is coplanar with the wicking member and sandwiched between the first layer and the testing members 108–112. In one embodiment, the wicking member is longer than the capillary transfer plane member so that sample application area 115 of wicking member 101 is exposed so that a sample can be placed thereon. In one embodiment, capillary transfer plane member 102 is fabricated from Mylar or other suitable material.

Figure 1:
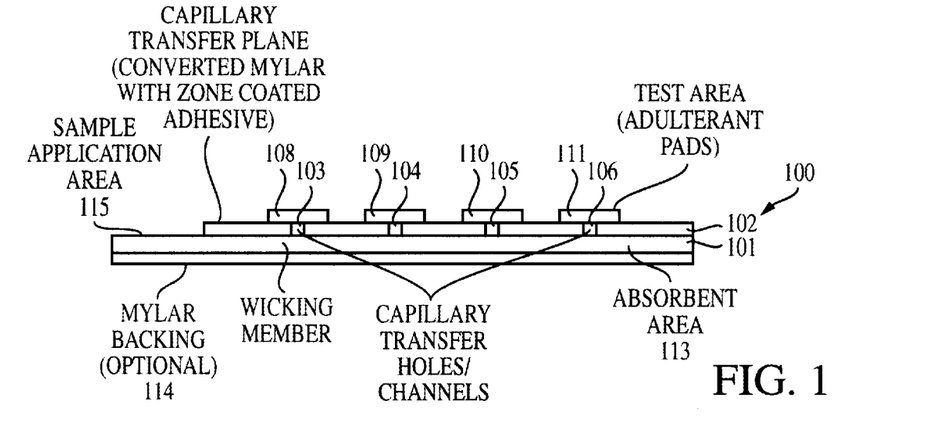
FIG. 1 shows a side view of one embodiment of a test strip according to the present invention.
Figure 2:
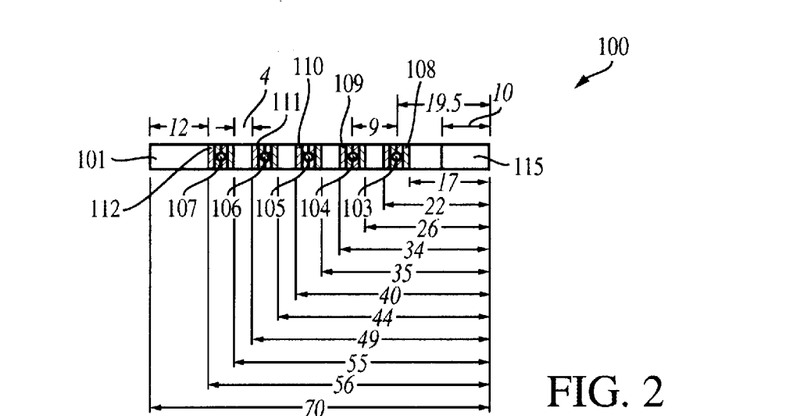
FIG. 2 shows a top view of the test strip of FIG. 1.
Figure 3:
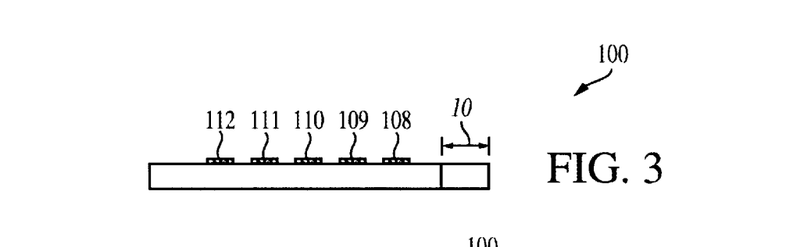
FIG. 3 is a side view of the test strip of FIG. 1.
Figure 4:
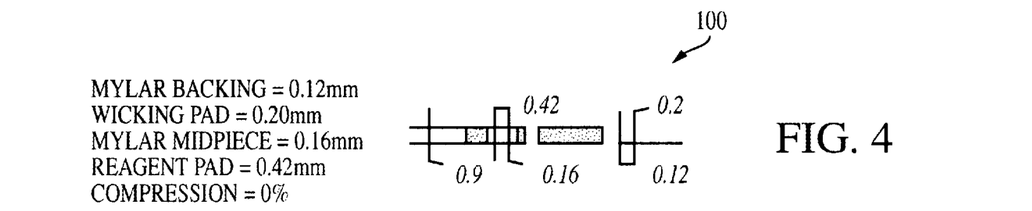
FIG. 4 is a front view of the test strip of FIG. 1.
Figure 5:
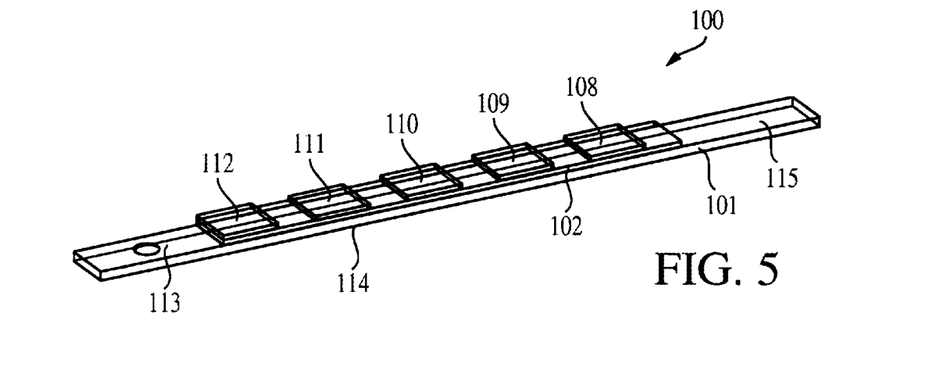
FIG. 5 is an isometric view of the test strip of FIG. 1.
Figure 6:
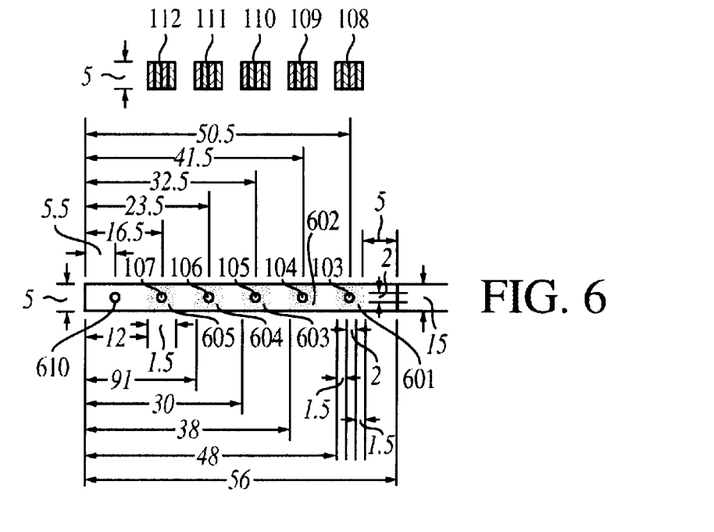
FIG. 6 is an exploded view of the test strip of FIG. 1.
Figure 8:
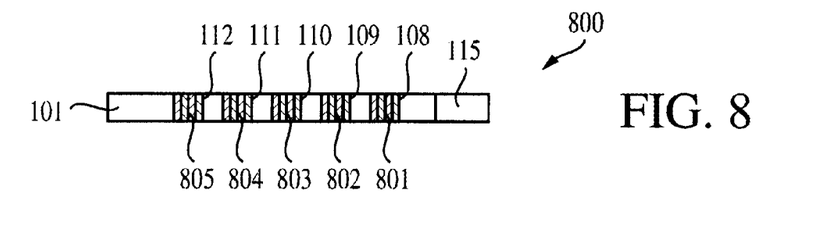
FIG. 8 is a top view of another embodiment of a test strip according to the present invention.

Member 102 includes a plurality of capillary transfer passages 103–107. These passages provide a capillary force action to draw a portion of a sample placed on wicking member 101 to be drawn upwards through the passage and into contact with the testing members 108–112. Each of the capillary transfer passages are of a suitable size for providing correct flow rate of the sample. In one embodiment, the passages are holes of approximately 0.5 to 2.5 millimeters in diameter. In another embodiment, each passage is a hole approximately 2 millimeters in diameter. Those skilled in the art will appreciate that the exact size of the hole is determined by the viscosity of the liquid and the desired flow rate. Moreover, it is noted that if the passage is too small, surface tension of the sample fluid will prevent flow and if the passage is too large, the capillary action will not be activated. Alternatively, the passages can be channels, such as channels 801–805 shown in FIG. 8. Alternatively, any other transfer means may be used instead of holes or channels, such as star-shaped holes or other shapes.

Figure 9:
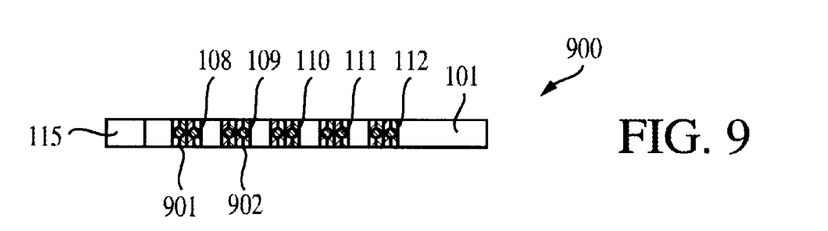
FIG. 9 is a top view of another embodiment of a test strip according to the present invention.
Figure 10:
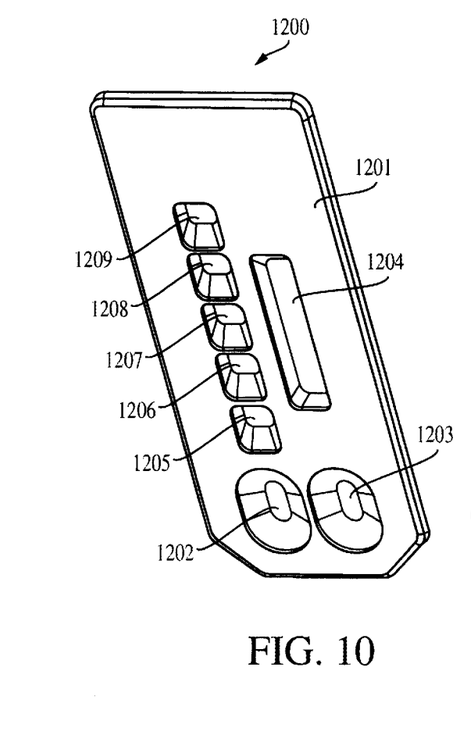
FIG. 10 is a front isometric view of one embodiment of a device carrier according to the present invention.
Figure 11:
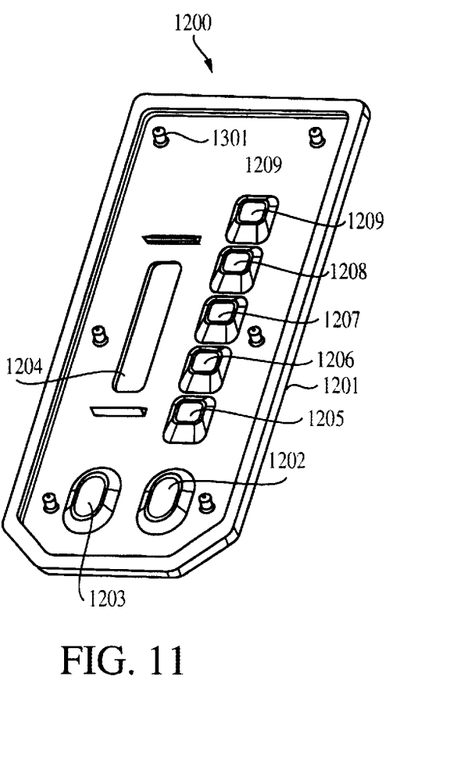
FIG. 11 is a back isometric view of the device carrier of FIG. 10.

Furthermore, more than one hole, channel, or other shaped passage may be located under each test area, as shown in FIG. 9, which shows a test strip 100 which includes a pair of holes 901 and 902 beneath each testing member 108–112. As noted above, the exact size, shape, and number of the capillary transfer passages depends on the viscosity of the fluid sample and the desired flow rate. Advantageously, the pressure at the inlet of a given capillary transfer passage 108–112 is sufficient to prevent an immediate back-flushing effect into the wicking member 101. This prevents any cross-contamination of or between the separate testing members 108–112. Such cross-contamination can be caused by the cross-mixing of the reagents on the pads or a combination of reagent and sample being reintroduced back to the main sample in the wicking member.

Figure 7:
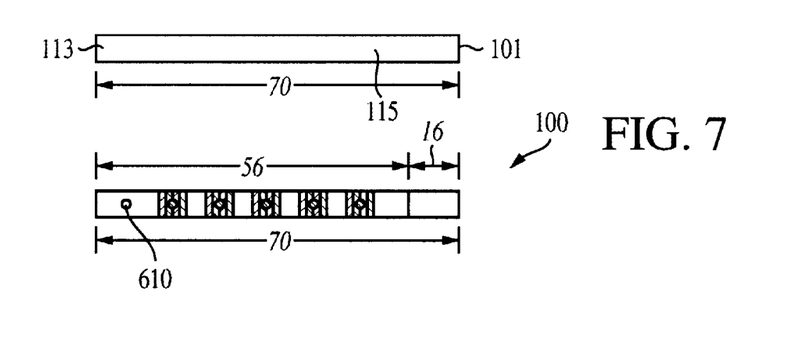
FIG. 7 is a top view of another embodiment of a test strip according to the present invention.

Also, the passages provide that test strip 100 does not have any testing reagents located on the wicking member 101 or on any material in direct contact with the wicking member. The testing reagents on the testing members 108–112 are isolated from the first layer containing the sample and they receive the necessary sample volume intermittently as the sample runs along the first layer material. Advantageously, this also prevents cross contamination which would result from a contrary system. In one embodiment, capillary transfer plane member 102 also includes an indexing hole 610 (see FIGS. 6 and 7). Indexing hole 610 provides a means during manufacturing for aligning passages 103–107 so that they are the proper distance apart.

The present invention is not limited by the size of the layers, and those skilled in the art will appreciate that a variety of sizes are within the scope of the present invention. However, by way of example, but not limitation, in one embodiment, the first layer, such as wicking member 101, is approximately 70 millimeters long by 5 millimeters wide and 0.20 millimeters thick. Also, way of example, but not limitation, in one embodiment, member 102 is approximately 56 millimeters long by 5 millimeters wide and 0.50 millimeters thick.

Testing members 108–112 are testing areas or test pads which are fabricated from porous materials that will hold specific testing reagents. The testing reagents in the testing members 108–112 can provide for separate testing of a single sample. In one embodiment, the testing members can include a color-coded, positive or negative, test result. The testing members are located over the capillary transfer passages 103–107 in the capillary transfer plane member 102. In one embodiment, member 102 includes adhesive zones 601–605 for attaching testing members 108–112 over its capillary transfer passages 103–107 (see FIG. 6). It is noted that the number of testing members shown in the Figures is exemplary, and that the present invention could include more or less, depending on the need.

As a sample flows along the wicking member 101, some of the sample will be pulled through the first capillary transfer passage 103 and saturate the first testing member 108. As noted above, the capillary transfer passages 103–107 are shaped and designed a suitable size for providing correct flow rate of the sample. The sample will continue on to each adjacent capillary transfer passage 104–107 in the same manner until it reaches the absorbent area 113. This system provides that a user need only add a few drops to the application area 115. This lessens the complexity of doing multiple tests since there is no need to carefully time the immersion of the test strip in the fluid sample. Also, since immersion is not required, the present system provides for a neater, more sanitary testing system.

Figures 12, 13:
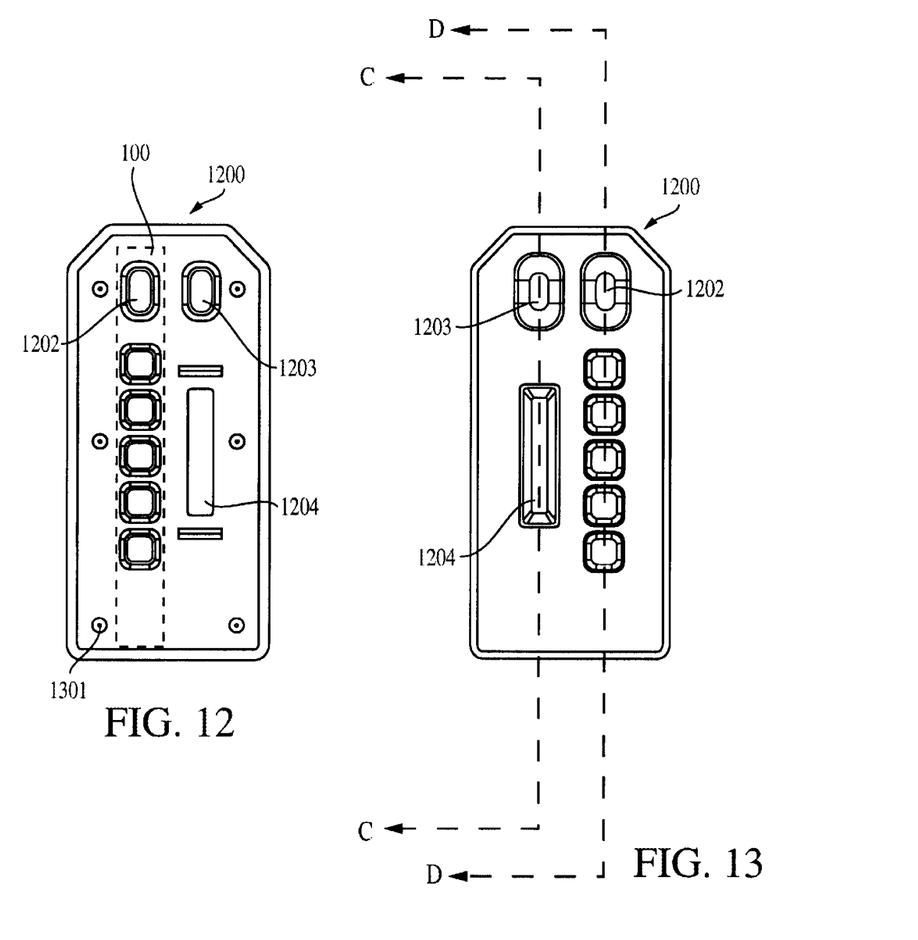
FIG. 12 is a back view of the device carrier of FIG. 10.
FIG. 13 is a front view of the device carrier of FIG. 10.
Figure 14:
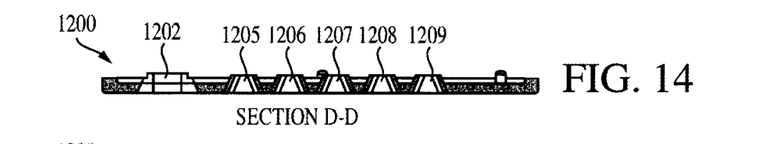
FIG. 14 is a sectional view of the device carrier of FIG. 10.
Figure 15:
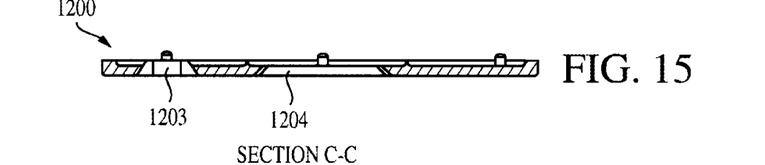
FIG. 15 is another sectional view of the device carrier of FIG. 10.

FIGS. 10–15 show one embodiment of a sample testing device comprising a carrier device or housing 1200 having a plurality of openings and a test strip 100 located within the housing (the test strip is shown in outline in FIG. 12. The test strip 100 is substantially as described above, and will not be described further). Housing 1200 includes a first, front member 1201 and a second member (not shown) which provides a backing for the housing. The front and back members can be attached by attaching members 1301. Housing 1200 also includes a plurality of openings, such as viewing openings 1205–1209 and sample application openings 1202 and 1203. The test strip is contained within carrier device 1200 so that each of the testing members 108–112 is viewable through at least one of the plurality of openings 1205–1209 of the housing 1200. In one example of using the present system for performing a test of a sample, the sample is deposited on the sample application area 115 of the test strip 100 through opening 1202 of the housing. In one embodiment, carrier device or housing 1200 can also include another sample opening 1203 and another viewing opening 1204. This provides that another type of testing system can be incorporated into the carrier device.

As will be recognized by one skilled in the art, the present invention relates generally to any dipstick format test whereby the sample must be introduced to the testing area by submerging the dipstick into the sample being tested or have the sample introduced directly onto the test areas. Advantageously, the lateral flow test strip 100 placed within the carrier device 1200 provides that a sample can be tightly controlled, isolated and identified, even after introducing the sample into the sample application area 115. For example, if multiple samples are being tested, as is the case in a laboratory environment, it is difficult to efficiently identify multiple samples from different patients once the samples are removed from a collection cup. Advantageously, in the present system, the lateral flow test strip in a carrier device provides an area for permanent and efficient sample/patient identification. Moreover, the present system can be used for the conversion of adulterant or urinalysis dipsticks that screen for adulterants in urine samples or uranalysis tests that screen for Ph factors, for example.

CONCLUSION

A sample testing system has been described. In one embodiment, the system includes a test strip 100 for testing a sample. Test strip 100 having a first layer, such as a wicking member 101, for holding and carrying the sample. The test strip includes a second layer next to the first layer comprising a capillary transfer plane member 102 having a plurality of capillary transfer passages 103–107 for drawing a portion of the sample away from the wicking member 101. The test strip also includes and a plurality of testing members 108–112, each testing member located over at least one of the plurality of capillary transfer passages, each testing member 108–112 for receiving the portion of the sample from the capillary passage(s) beneath the testing member. In one embodiment, the wicking member 101 comprises a first end having a sample application area 115 and a second end comprising an absorbent area 113. In one embodiment, the capillary transfer passages comprises a hole of approximately 0.5 to 2.5 millimeters in diameter. Alternatively, the capillary passage can be shaped as a channel, star, or other shape to provide the correct flow depending on the flow rate desired by the designer. Each of the plurality of testing members 108–112 comprise a porous material holding a testing reagent.

In another aspect, the present system provides a lateral flow test strip 100 that can be placed into a carrier device 1200 or instrument to assist in handling and containing the sample being tested, such as urine, blood, body fluids or any other type of sample extraction. The lateral flow test strip 100 provides a method for converting any type of dipstick style test, such as adulterants, glucose, urinalysis, etc. to an easy and sanitary format by enclosing and controlling the sample. The present invention makes the testing process easier, more sanitary, and less confusing when processing multiple samples.

It is understood that the above description is intended to be illustrative, and not restrictive. Many other embodiments will be apparent to those of skill in the art upon reviewing the above description. The scope of the invention should, therefore, be determined with reference to the appended claims, along with the fill scope of equivalents to which such claims are entitled.

What is claimed is:

1. A test strip for testing for a substance in a sample, comprising:
   a first layer adapted for drawing sample from a first end of the first layer to a second end of the first layer;
   a second layer coplanar with the first layer, the second layer comprising a capillary transfer plane member comprised of a material through which fluid will not flow and having a plurality of capillary transfer passages, each transfer passage having a first and second end, the first end being located in fluid contact with the first layer; and
   a plurality of testing members, each testing member being in fluid contact with the second end of one of the plurality of capillary transfer passages of the second layer, the size and length of each transfer passage being chosen to allow a quantity of sample to be drawn through the transfer passage to the testing member from the first layer, and wherein the plurality of testing members are arranged in a linear sequence and wherein the sample placed on the first end of the first layer reaches each of the plurality of testing members sequentially.

2. The test strip of claim 1, wherein the first layer comprises a wicking member.

3. The test strip of claim 1, further comprising a third layer, the third layer located next to the first layer, opposite the second layer, and wherein the third layer comprises a backing member.

4. The test strip of claim 1, wherein each of the plurality of capillary transfer passages comprises an opening defined in the capillary transfer plane member.

5. The test strip of claim 1, wherein each of the plurality of capillary transfer passages comprises a channel.

6. The test strip of claim 1, wherein the first layer comprises a wicking member, and wherein the first end of said wicking member comprises a sample application area and the second end comprises an absorbent area.

7. The test strip of claim 1, wherein each testing member comprises a porous material holding a testing reagent chosen for detecting the substance in the sample.

8. The test strip of claim 1, wherein each of the capillary transfer passages comprises an opening with a diameter of approximately 0.5 to 2.5 millimeters defined in the capillary transfer plane member.

9. The test strip of claim 1, wherein each of the capillary transfer passages comprises a channel of approximately 2 millimeters in width.

10. A test strip for testing a sample, comprising:
    a first layer adapted to draw the sample from a first end of the first layer to a second end of the first layer;
    a second layer comprising a capillary transfer plane member comprised of a material through which fluid will not flow and having a plurality of capillary transfer passages, each capillary transfer passage being adapted to draw a portion of the sample away from the first layer; and
    a plurality of testing members comprising a reagent for testing the sample, each testing member located over and in fluid contact with at least one capillary transfer passage, each testing member positioned to receive the portion of the sample drawn away from the first layer by the capillary transfer passage beneath the testing member,
    wherein each of the capillary transfer passages is sized in length and volume so that backflow of the sample and reagent from the testing member in fluid contact with the capillary transfer passage towards the first layer is prevented.

11. The test strip of claim 10, wherein the first layer comprises a wicking member.

12. The test strip of claim 11, wherein each of the capillary transfer passages comprises an opening with a diameter of approximately 0.5 to 2.5 millimeters defined by the capillary transfer plane member.

13. The test strip of claim 11, wherein each of the plurality of capillary transfer passages comprises a channel.

14. The test strip of claim 11, further comprising a backing member for providing support to the wicking member.

15. The test strip of claim 11, wherein the wicking member comprises a first end for applying the sample to the test strip and a second end comprising an absorbent area for causing the sample to flow laterally down the wicking member.

16. A test strip for testing a sample, comprising:
    a first layer comprising a wicking member for carrying the sample, the wicking member comprising a first end having a sample application area and a second end comprising an absorbent area wherein the sample flows laterally through the wicking member from the first end to the second end;

a second layer comprising a polyester film layer attached by an adhesive to the first layer and coplanar with the first layer, the second layer having a plurality of capillary transfer passages, each capillary transfer passage adapted to draw a portion of the sample away from the wicking member; and a plurality of testing members, each testing member located over and in fluid contact with at least one of the plurality of capillary transfer passages, each of the plurality of testing members comprising a porous material holding a testing reagent.

17. The test strip of claim 16, wherein each of the capillary transfer passages comprises an opening with a diameter of approximately 0.5 to 2.5 millimeters defined in the second layer.

18. The test strip of claim 16, wherein each of the plurality of capillary transfer passages comprises a channel.

19. The test strip of claim 16, further comprising a backing member for providing support to the wicking member on the side of the wicking member opposite the second layer.

20. A sample test device, comprising:

a housing adapted to hold and display test strips having a first opening and a second opening; and first and second test strips located within the housing, wherein the first test strip is viewable through the first opening and the second test strip is viewable through the second opening;

wherein the first test strip comprises an adulterant test strip and the second test strip comprises a drug-test strip.

21. The sample testing device of claim 20, wherein the adulterant test strip includes:

a first layer;

a second layer located next to the first layer, the second layer comprising a capillary transfer plane member coplanar with the first layer comprised of a material through which fluid will not flow and having a plurality of capillary transfer passages; and a plurality of testing members each comprising a testing reagent and each testing member being located over and in fluid contact with at least one of the plurality of capillary transfer passages.

22. The sample testing device of claim 21, wherein the first layer comprises a wicking member, the wicking member having a first end comprising a sample application area and a second end comprising an absorbent area, wherein the sample applied to the sample application area will flow laterally through the wicking member to the second end and further comprising a third opening in the housing through which the sample application area is accessible.

23. The sample testing device of claim 21, wherein each of the capillary transfer passages comprises an opening with a diameter of approximately 0.5 to 2.5 millimeters defined in the second layer.

24. The sample testing device of claim 21, wherein each of the capillary transfer passages comprises a channel having a width of approximately 2.0 millimeters.

25. A method of performing a test of a sample, the method comprising:

providing a test strip having a wicking member through which sample applied to the test strip will laterally flow and at least one testing member, wherein the wicking member and the at least one testing member are separated by a member comprised of a material through which fluid will not flow having a capillary transfer passage, the member between the wicking member and the testing member being sized and positioned so that a portion of the sample will flow through the capillary transfer passage from the wicking member to the testing member but none of the sample will flow directly from the testing member to the wicking member; and depositing the sample onto the wicking member of the test strip.

26. The method of claim 25, further comprising mounting the test strip within a housing adapted to hold and display the test strip before depositing the sample.

27. A sample testing device, comprising:

a housing having walls defining a plurality of openings; and a test strip located within the housing, the test strip comprising:

a first layer;

a second layer located next to and coplanar with the first layer, the second layer comprising a capillary transfer plane member comprised of a material through which fluid will not flow and having a plurality of capillary transfer passages; and a plurality of testing members, each testing member located over and in fluid contact with at least one of the plurality of capillary transfer passages, each of the testing members viewable through at least one of the plurality of openings in the housing;

wherein the housing includes a portion for providing pressure along a longitudinal section of the test strip sufficient to prevent backflow and to facilitate fluid flow to each testing member from the capillary transfer passages.

28. The sample testing device of claim 27, wherein the test strip comprises an adulterant test strip.

29. A test strip for testing a sample comprising:

a first layer through which sample laterally flows;

a second layer located next to and coplanar with the first layer, the second layer comprising a capillary transfer plane member comprised of a material through which fluid will not flow and having a plurality of capillary transfer passages in fluid contact with the first layer defined in the capillary transfer plane member; and a plurality of testing members, each testing member located over and in fluid contact with at least one of the plurality of capillary transfer passages, wherein each of the capillary transfer passages comprises a channel having a width of approximately 2.0 millimeters.

30. The test strip of claim 29, wherein the first layer comprises a wicking member.

31. The test strip of claim 29, further comprising a third layer, the third layer being located next to the first layer opposite the second layer, the third layer comprising a backing member.

* * * * *

UNITED STATES PATENT AND TRADEMARK OFFICE
CERTIFICATE OF CORRECTION

PATENT NO. : 6,566,051 B1
DATED : May 20, 2003
INVENTOR(S) : Owens et al.

It is certified that error appears in the above-identified patent and that said Letters Patent is hereby corrected as shown below:

<u>Title page,</u>
Items [75] and [12] should read:
-- [12] United States Patent
      Owens et al. --
-- [75] Inventors: Mitchell Owens, Greensboro, NC (US)
              Norman S. Reddick Jr., Liberty, NC (US)
              Michael Turanchik, Gibsonville, NC (US) --

Signed and Sealed this

Twenty-third Day of September, 2003

JAMES E. ROGAN
*Director of the United States Patent and Trademark Office*